(12) United States Patent
Villaseca et al.

(10) Patent No.: US 7,486,184 B2
(45) Date of Patent: *Feb. 3, 2009

(54) COAXIAL CABLE ANTENNA FOR COMMUNICATION WITH IMPLANTED MEDICAL DEVICES

(75) Inventors: Eduardo H. Villaseca, Minneapolis, MN (US); Bonnie Dougherty, legal representative, Minneapolis, MN (US); Garry L. Dublin, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 214 days.

This patent is subject to a terminal disclaimer.

(21) Appl. No.: 11/199,109

(22) Filed: Aug. 8, 2005

(65) Prior Publication Data

US 2005/0270245 A1  Dec. 8, 2005

Related U.S. Application Data

(63) Continuation of application No. 10/423,666, filed on Apr. 25, 2003, now Pat. No. 6,930,602.

(51) Int. Cl.
*G08B 1/08* (2006.01)
*A61B 5/00* (2006.01)
*H01Q 1/00* (2006.01)

(52) U.S. Cl. .................. 340/539.12; 340/539.1; 340/573.1; 600/301; 607/32; 128/903; 343/720

(58) Field of Classification Search ............ 340/539.12; 607/60
See application file for complete search history.

(56) References Cited

U.S. PATENT DOCUMENTS

| 4,953,197 | A | | 8/1990 | Kaewell, Jr. et al. |
| 5,748,103 | A | * | 5/1998 | Flach et al. ............ 340/870.07 |
| 5,904,708 | A | * | 5/1999 | Goedeke ...................... 607/18 |
| 5,944,659 | A | * | 8/1999 | Flach et al. .................. 600/300 |
| 6,169,925 | B1 | | 1/2001 | Villaseca et al. |
| 6,448,933 | B1 | | 9/2002 | Hill et al. |
| 6,456,245 | B1 | | 9/2002 | Crawford |
| 6,526,310 | B1 | * | 2/2003 | Carter et al. ................ 600/509 |
| 6,567,703 | B1 | * | 5/2003 | Thompson et al. ............ 607/60 |
| 6,930,602 | B2 | * | 8/2005 | Villaseca et al. ....... 340/539.12 |

\* cited by examiner

*Primary Examiner*—Donnie L Crosland
(74) *Attorney, Agent, or Firm*—Michael C. Soldner

(57) ABSTRACT

A coaxial cable antenna is provided for use in an external device, such as a programmer or monitor, to enhance communication between the external device and an implanted medical device (IMD). The coaxial cable antenna provides the external device with polarization diversity. For example, the coaxial cable antenna includes a first portion and a second portion that are substantially perpendicular to one another. Each of the portions of the coaxial cable antenna has a different polarization orientation, thus providing the programmer with polarization diversity. Further, the external device may include more than one coaxial cable antenna to provide the external device with spatial diversity as well as polarization diversity provided by the coaxial cable antenna design. The coaxial cable antenna configurations reduce problems associated with polarization mismatches, antenna nulls, and multi-path propagation interference.

45 Claims, 4 Drawing Sheets

COAXIAL CABLE ANTENNA FOR COMMUNICATION WITH IMPLANTED MEDICAL DEVICES

PRIOR APPLICATION

This application is a continuation application of prior application Ser. No. 10/423,666, filed Apr. 25, 2003, entitled "Coaxial Cable Antenna for Communication with Implanted Medical Devices," now U.S. Pat. No. 6,930,602.

TECHNICAL FIELD

The invention relates to wireless communication between an implanted medical device (IMD) and an external programmer or monitor and, more particularly, to antennas for use with the external programmer or monitor.

BACKGROUND

An implanted medical device (IMD) and an external device, such as a programmer or monitor, exchange information via wireless communication. For example, the external device typically transmits commands to the IMD. In addition, the IMD transmits stored information or sensed physiological parameters to the external device.

The external device typically includes a programming head containing an antenna for wireless communication with an antenna in the IMD. In operation, the programming head is placed in close proximity to the IMD to establish data communication with the IMD.

SUMMARY

In general, the invention is directed to a coaxial cable antenna for use in an external device, such as a programmer or monitor, to enhance communication between the external device and an implanted medical device (IMD).

In accordance with the invention, the external device includes two coaxial cable antennas for communication with the IMD. The coaxial cable antenna is constructed to provide polarization diversity, which allows the antenna to operate effectively in different planes. In order to achieve polarization diversity, the two antennas are arranged orthogonal to one another. The external device includes the two coaxial cable antennas to provide the external device with spatial diversity as well as polarization diversity provided by the coaxial cable antenna design. For example, a programmer for an IMD includes a first coaxial cable antenna, a second coaxial cable antenna, and a receiver that receives signals from the IMD via one of the first or the other coaxial cable antennas. The programmer includes a display, and the coaxial cable antennas are mounted within a housing of the display to protect the coaxial cable antennas from the surrounding environment. In other words, the display housing is part of and protects the coaxial cable antennas from incidental contact that could otherwise bend or break the antennas.

The coaxial cable antennas can be mounted proximate upper corners of the display. Specifically, the first coaxial cable antenna is located proximate a top left corner of the display and the second coaxial cable antenna is located proximate a top right corner of the display. Each of the coaxial cable antennas includes a first portion substantially parallel to a side of the display and a second portion substantially parallel to a top of the display. The portion of each coaxial cable antennas parallel with the side of the display has a first polarization and the portion of each coaxial cable antennas parallel with the top of the display has a second polarization. In other words, each of the portions of the coaxial cable antennas has a different polarization orientation, thus providing the programmer with polarization diversity.

In addition, the coaxial cable antennas are spaced approximately half of a wavelength apart from one another to achieve spatial diversity. However, the coaxial cable antennas could be spaced approximately one-quarter of a wavelength apart from one another. In this manner, the coaxial cable antennas receive signals from the IMD over multiple different receive paths providing a programmer or monitor with spatial diversity as well as the polarization diversity provided by the coaxial cable antenna design.

Each of the coaxial cable antennas includes a center conductor that carries signals received from the IMD or signals to be transmitted to the IMD, surrounded by an insulator and an outer conductive cladding surrounding the center conductor. In accordance with the invention, a portion of the outer conductive cladding is removed to expose the insulator of the coaxial cable antenna.

The portion of the removed outer conductive cladding is located near a midpoint of the coaxial cable antennas. Further, a portion of the exposed insulator is removed to expose the center conductor of coaxial cable antennas. A resistor and a capacitor are connected between the center conductor and the outer conductive cladding.

The capacitor is connected between the center conductor and the outer conductive cladding in order to adjust the voltage standing wave ratio (VSWR) at an operating frequency of the coaxial cable antennas. The resistor is also connected between the center conductor and the outer conductive cladding to lower the quality factor (Q) of the coaxial cable antennas, in turn, increasing the bandwidth of the coaxial cable antennas.

Each coaxial cable antenna further includes a hole that extends through the outer conductive cladding and cuts through the center conductor at a specific location to tune the operating frequency of the coaxial cable antenna. The hole may be placed such that the operating frequency of the coaxial cable antennas tune to approximately 400 Megahertz (MHz) and, more specifically, approximately 403 MHz.

In one embodiment, the invention provides an external device that communicates with an implanted medical device, the external device comprising a first coaxial cable antenna, a second coaxial cable antenna, and a receiver that receives signals from the implanted medical device via at least one of the first and second coaxial cable antennas.

In another embodiment, the invention is directed to an external device that communicates with an implanted medical device, the external device comprising a plurality of coaxial cable antennas, a receiver to receive signals from the implanted medical device via at least one of the coaxial cable antennas, and a device housing, the coaxial cable antennas mounted within the device housing.

In a further embodiment, the invention is directed to a method comprising receiving signals from an implanted medical device via a plurality of coaxial cable antennas and processing the signals from the implanted medical device to analyze information from the implanted medical device.

The details of one or more embodiments of the invention are set forth in the accompanying drawings and the description below. Other advances and inventive aspects of the invention will be apparent from the description and drawings, and from the claims.

DETAILED DESCRIPTION

Figure 1:
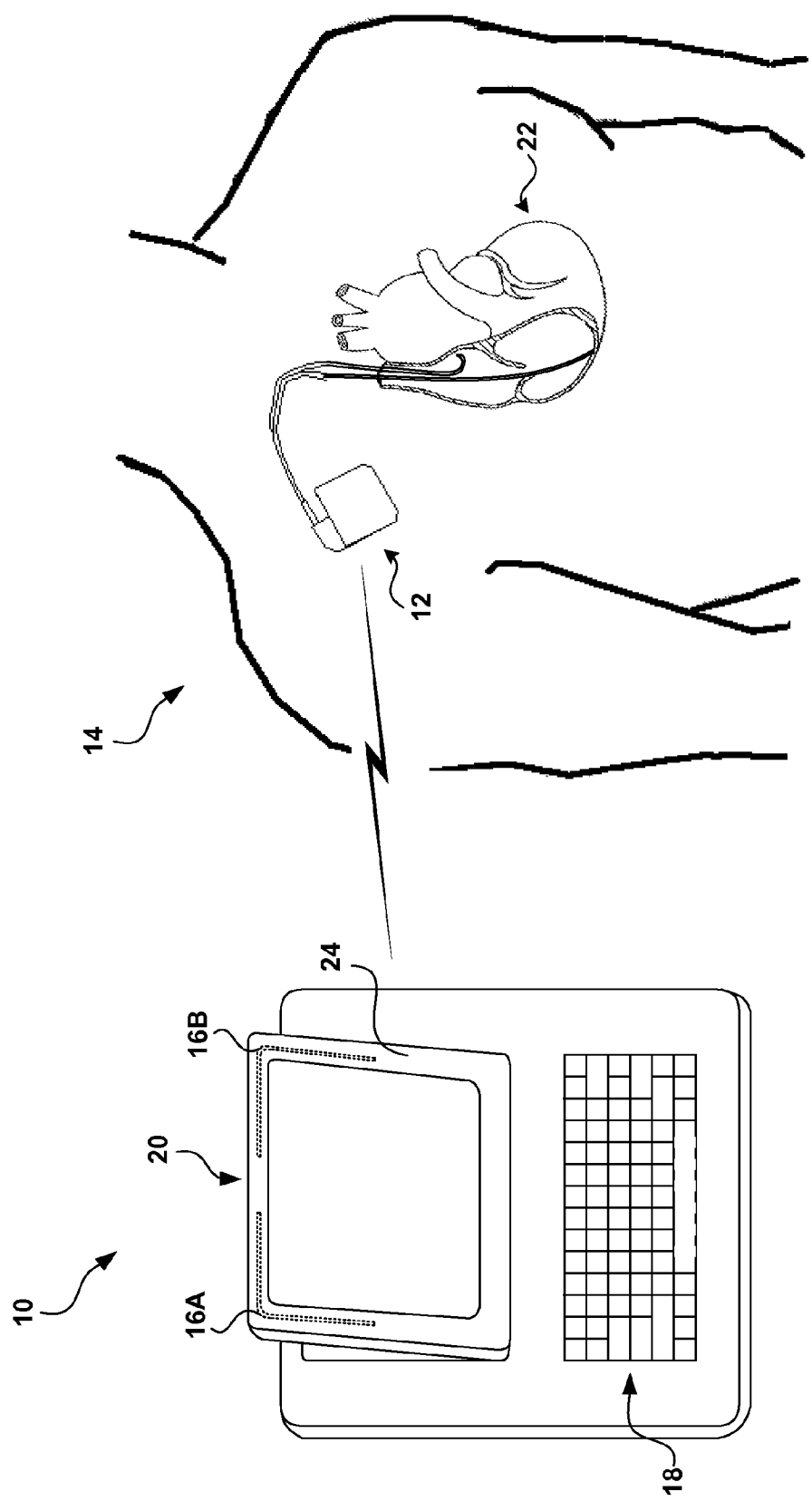
FIG. 1 is a perspective diagram illustrating an external device that communicates with an implantable medical device (IMD) implanted within a patient.

FIG. 1 is a perspective diagram illustrating an external device, e.g., a programmer 10, that communicates with an implantable medical device (IMD) 12 implanted within a patient 14. In accordance with the invention, programmer 10 includes coaxial cable antennas 16A and 16B (hereinafter 16) arranged to provide programmer 10 with spatial as well as polarization diversity. Programmer 10 transmits commands to IMD 12 and receives stored operational information and physiological information from IMD 12.

IMD 12 may be an implantable pulse generator (IPG), e.g., a pacemaker, or an implantable cardioverter-defibrillator (ICD). However, programmer 10 may be used to communicate with any type of IMD 12. Other examples of IMD 12 include an implantable brain stimulator, an implantable gastric system stimulator, an implantable nerve stimulator or muscle stimulator, an implantable lower colon stimulator, urinary tract stimulator, an implantable drug or beneficial agent dispenser or pump, an implantable cardiac signal loop or other type of recorder or monitor, an implantable gene therapy delivery device, an implantable incontinence prevention or monitoring device, an implantable insulin pump or monitoring device, and the like.

Further, although described in terms of a programmer 10 for purposes of illustration, the antenna configurations described herein may be used in other external devices that communicate with an IMD 12 such as a patient monitoring device, which may not have programming capabilities. In each case, the external device communicates with IMD 12 to obtain operational and physiological information. IMD 12 collects operational information and physiological information. Depending on the type of IMD 12, the physiological information may include heart rate, heart rate variability, blood glucose levels, oxygen saturation, partial pressure of oxygen in the blood, blood pressure, baro-reflex measures, electrogram morphologies, lung wetness, and the like.

A user (not shown) of programmer 10, such as a clinician or physician, interacts with programmer 10 and IMD 12 via an input medium, such as keyboard 18, and a display 20. More specifically, programmer 10 provides a user interface that the user interacts with to provide data to programmer 10. Display 20 may for example, be a Cathode Ray Tube (CRT) display, Liquid Crystal Display (LCD), Light-Emitting Diode (LED) display, a plasma display or the like. In some embodiments, programmer 10 also includes a pointing device, such as a mouse, via which the user interacts with the user interface. Further, programmer 10 may include a touch screen or other similar input medium to interact with the user.

Programmer 10 is in wireless communication with IMD 12. Programmer 10 communicates with IMD 12 by wireless transmission via coaxial cable antennas 16, constructed in accordance with the invention. Coaxial cable antennas 16 are mounted within a housing 24 of display 20 to protect coaxial cable antennas 16 from the surrounding environment. In other words, housing 24 of display 20 prevents coaxial cable antennas 16 from incidental contact that may otherwise bend or break antennas external to programmer 10. In some embodiments, coaxial cable antennas 16 may be external coaxial cable antennas coaxial cable antennas connected to programmer 10 via a cable. Housing 24 to which coaxial cable antennas 16 are mounted is fabricated from a non-conductive material, such as plastic. Display 24 also includes a conductive backplane that is constructed of a metal or metalized plastic. As will be described, coaxial cable antennas 16 are arranged to provide spatial diversity as well as polarization diversity, in turn allowing programmer 10 to communicate with IMD 12 from several feet or meters away. Coaxial cable antennas 16 reduce problems associated with polarization mismatches, antenna nulls, and multi-path interference.

Programmer 10 interrogates IMD 12 to retrieve measured data, along with currently programmed parameters and optimization target values stored by IMD 12 via coaxial cable antennas 16. If IMD 12 is a pacemaker, the data retrieved includes data reflecting electrical activity sensed in heart 22, the output of various other sensors of IMD 12, such as one or more sensors used to control the rate response of IMD 12, and the rate response of IMD 12 over time. Programmer 10 displays some or all of these items to the user via display 20. The user further programs or reprograms IMD 12 via the user interface and input medium, e.g., keyboard 18. For example, the user provides or adjusts rate response parameters or target values of IMD 12 via the user interface and input medium, which are then relayed by programmer 10 to IMD 12 via a transmitter and coaxial cable antennas 16.

Figure 2:
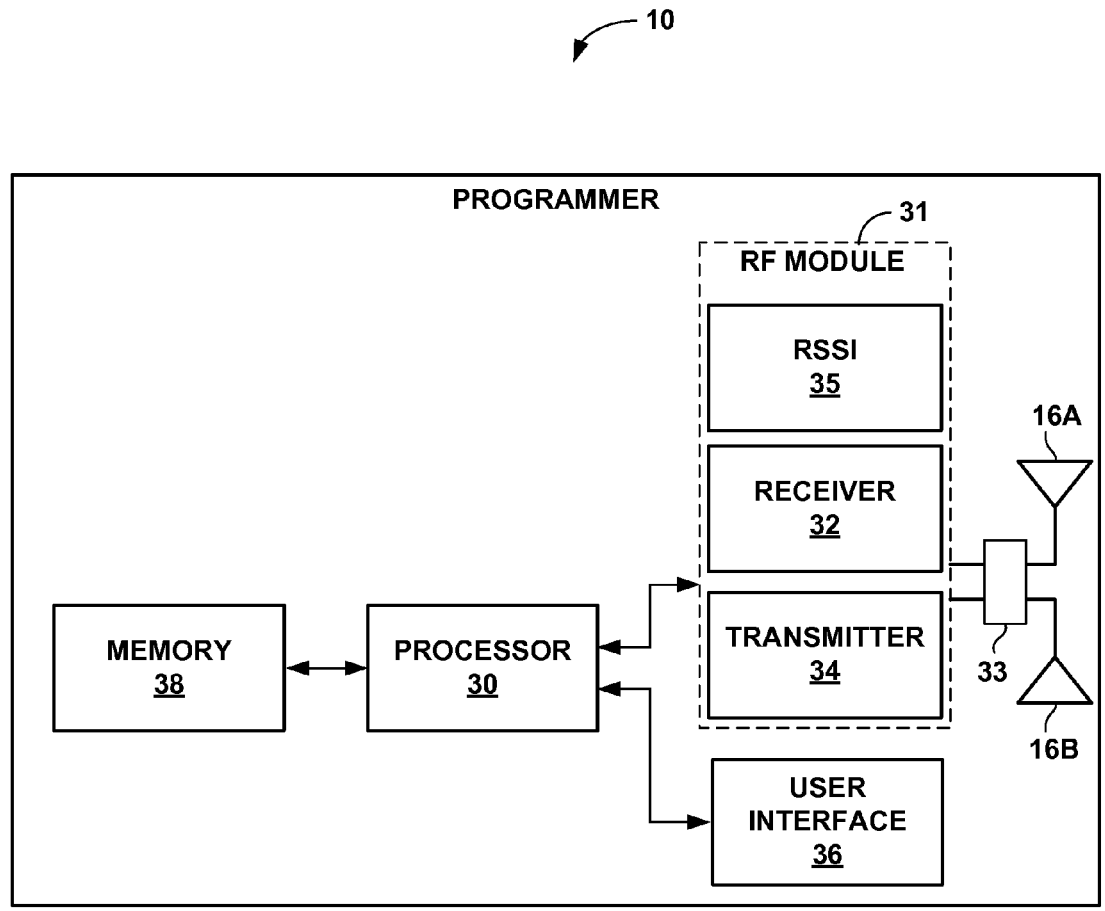
FIG. 2 is a block diagram illustrating the programmer of FIG. 1 in greater detail.

FIG. 2 is a block diagram illustrating programmer 10 in greater detail. As shown in FIG. 2, programmer 10 includes a processor 30, a radio frequency (RF) module 31, an antenna switch 33 controlled via a received signal strength indicator (RSSI) 35 and coaxial cable antennas 16A and 16B (hereinafter 16). As mentioned above, programmer 10 is in wireless communication with IMD 12. Particularly, programmer 10 transmits and receives signals to and from IMD 12 via coaxial cable antennas 16. Coaxial cable antennas 16 are spaced substantially half of a wavelength, but could work with one quarter of a wavelength, from one another to receive signals from IMD 12 over multiple receive paths providing programmer 10 with receive diversity, thereby reducing multi-path propagation interference as well as antenna nulls. For example, coaxial cable antenna 16A provides a first receive path and coaxial cable antenna 16B provides a second receive path. More than two coaxial cable antennas 16 may be provided in some embodiments for enhanced receive diversity.

Programmer 10 selects, via antenna switch 33 and RF module 31, the receive path with the strongest signal. More specifically, RF module 31 includes a receiver 32 and RSSI 35 that selects the receive path with the strongest signal. Processor 30 receives data collected by IMD 12 and currently programmed parameters from IMD 12 via receiver 32 and one of coaxial cable antennas 16 and processes the data. RF module 31 further includes a transmitter 34, which allows programmer 10 to program IMD 12, e.g., to program new parameters and/or optimization target values of IMD 12, via coaxial cable antennas 16. Programmer 10 transmits signals to IMD 12 via one of coaxial cable antennas 16. Although in the example illustrated in FIG. 2 RF module 31 includes distinct components for receiving and transmitting signals, i.e., receiver 32 and transmitter 34, RF module 31 may include a single transceiver component that includes receive circuitry as well as transmit circuitry.

As discussed above, programmer 10 provides a user interface 36 by which a user of programmer 10, such as a clinician or physician, interacts with programmer 10 and IMD 12. In the example of FIG. 2, user interface 36 is a graphical user interface (GUI) displayed on display 20. A user interacts with user interface 36 via display 20 and at least one input medium such as keyboard 18, a pointing device, e.g., mouse, or a touch screen. A memory 38 stores program code that causes processor 30 to drive user interface 36, and the functionality ascribed to user interface 36. Memory 38 may include any fixed or removable magnetic or optical media, such as RAM, ROM, CD-ROM, hard or floppy magnetic disks, EEPROM, or the like.

Figure 3:
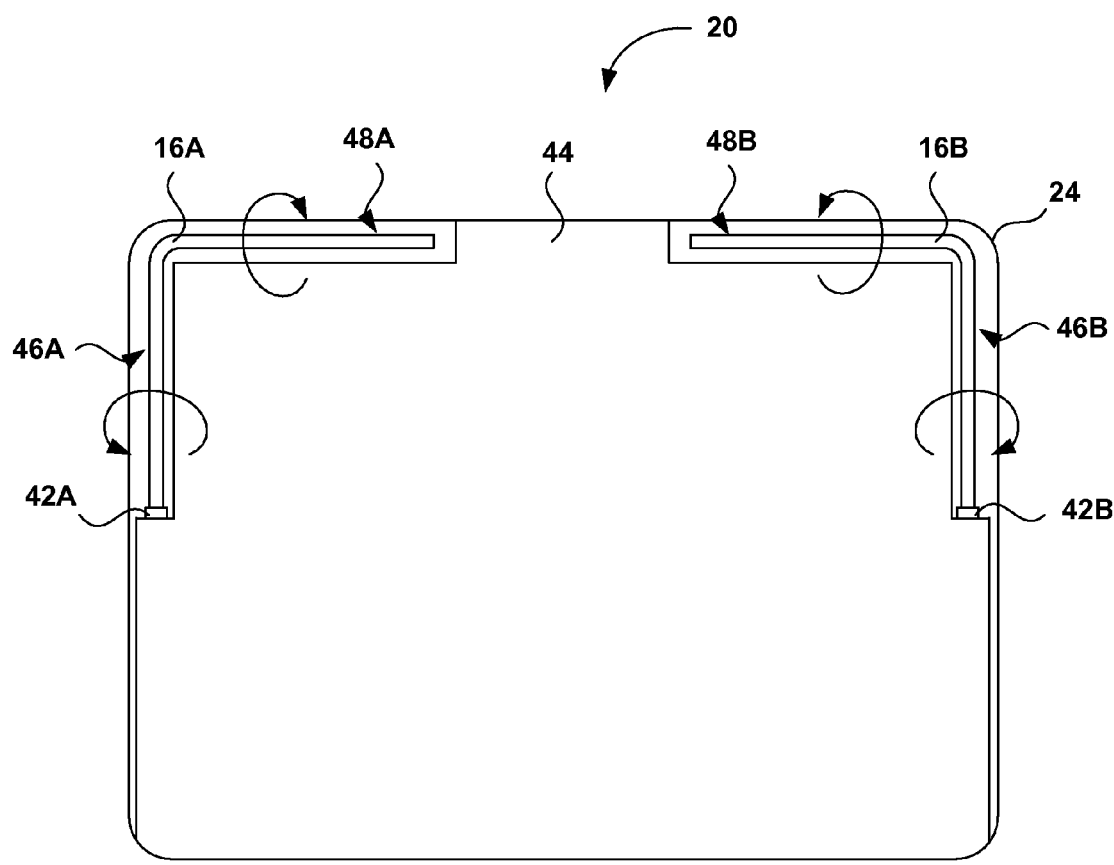
FIG. 3 is a schematic diagram illustrating a display of a programmer with a front portion of a housing removed to illustrate an interior of the display.

FIG. 3 is a schematic diagram illustrating display 20 with a front portion of housing 24 removed to illustrate the interior of display 20. Display 20 includes coaxial cable antennas 16A and 16B (hereinafter 16), connectors 42A and 42B (hereinafter 42), and a casting 44. As described above, coaxial cable antennas 16 are located within non-conductive housing 24 to protect coaxial cable antennas 16 from inadvertent damage caused by the surrounding environment. In some embodiments, coaxial cable antennas 16 are attached to housing 24 via one or more fasteners. Housing 24 further covers casting 44 to protect casting 44 from the surrounding environment. As described above, housing 24 is constructed from a non-conductive material such as plastic. In some embodiments, casting 44 is constructed of a conductive material, e.g., metal, and electromagnetically couples to coaxial cable antennas 16 in order to aid in tuning and impedance matching.

As illustrated in the example of FIG. 3, coaxial cable antennas 16 are mounted proximate top corners of display 20. Specifically, coaxial cable antenna 16A is located proximate a top left corner of display 20 and coaxial cable antenna 16B is located proximate a top right corner of display 20. Coaxial cable antennas 16 are substantially L-shaped to fit in the respective corners of display 20 and produce polarization diversity as described herein. In other words, each of coaxial cable antennas 16 includes a first portion 46 substantially parallel to a side of display 20 and a second portion 48 substantially parallel to a top of display 20 in accordance with the invention. Portion 46 of coaxial cable antennas 16 has a first polarization and portion 48 of coaxial cable antennas 16 has a second polarization. More specifically, portion 46 of coaxial cable antennas 16 has a horizontal elliptical or circular polarization (indicated by arrow 52), while portion 48 of coaxial cable antennas 16 has a vertical elliptical or circular polarization (indicated by arrow 54). In this manner, coaxial cable antennas 16 provide programmer 10 with polarization diversity. In other words, programmer 10 and, more particularly coaxial cable antennas 16, receive and transmit signals with horizontal polarization as well as vertical polarization, thus reducing antenna pattern nulls due to polarization mismatches.

Coaxial cable antennas 16 are further spaced a fraction of a wavelength, e.g., half of a wavelength, apart from one another to achieve spatial diversity. Coaxial cable antennas 16 may, for example, be spaced one-quarter of a wavelength apart from one another. In this manner, coaxial cable antennas 16 receive signals from IMD 12 over multiple receive paths, providing programmer 10 with spatial and polarization diversity, and thereby reducing multi-path propagation interference and antenna nulls. In contrast to wands and other programmer heads that are generally placed in close proximity to the body of the patient to communicate with IMD 12, the diversity arrangement of coaxial cable antennas 16, e.g., the spatial and polarization diversity, enable reception of signals from IMD 12 over extended distances such as several feet or meters from the IMD 12

Coaxial cable antennas 16 are attached to connectors 42 in order to conductively connect coaxial cable antennas 16 with RF module 31. More specifically, connectors 42 connect a center conductor of coaxial cable antennas 16 with receiver 32 or transmitter 34 via RSSI 35. In this manner, signals received by coaxial cable antennas 16 from IMD 12 are relayed to RF module 31 and signals from RF module 31 are relayed to coaxial cable antennas 16 for transmission to IMD 12.

Figure 4:
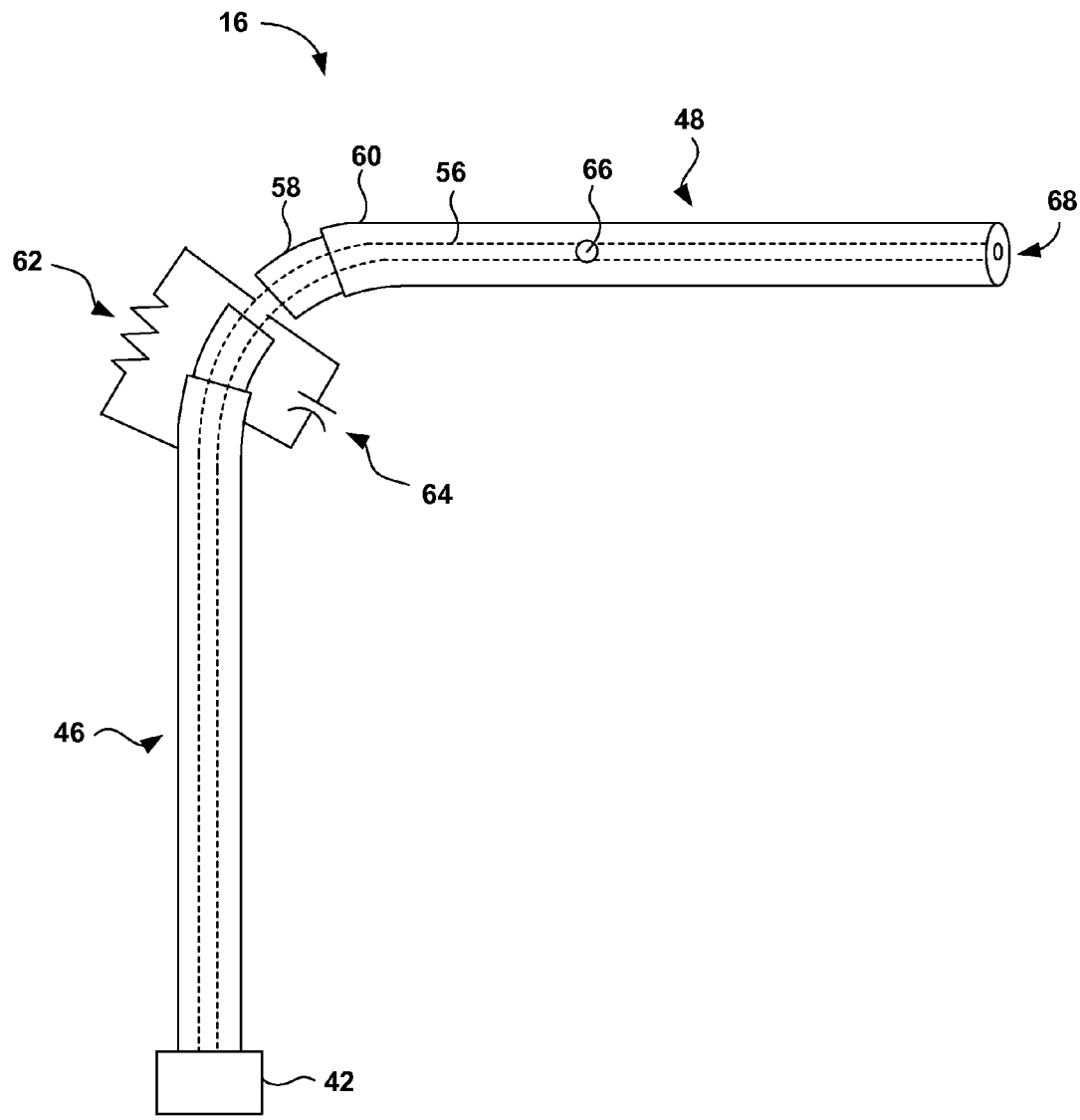
FIG. 4 is a schematic diagram illustrating a coaxial cable antenna in accordance with the invention.

FIG. 4 is a schematic diagram illustrating a coaxial cable antenna 16 in further detail. Coaxial cable antenna 16 is connected via a connector 40 to RF module 31 and, more particularly, to receiver 32, transmitter 34 or a transceiver of RF module 31. Coaxial cable antenna 16 includes a first portion 46 and a second portion 48 that are substantially perpendicular to one another to provide polarity diversity. As described above, portion 46 of coaxial cable antenna 16 is substantially parallel with a side of display 20 and portion 48 of coaxial cable antenna 16 is substantially parallel with a top of display 20. In this manner, coaxial cable antenna 16 radiate and tune signals with different polarizations, which permits display 20 to be oriented in numerous ways with respect to IMD 12. More specifically, portion 46 provides coaxial cable antenna 16 with a horizontal elliptical or circular polarization, while portion 48 of coaxial cable antenna 16 provides a vertical elliptical or circular polarization.

Coaxial cable antenna 16 includes a center conductor 56 that carries signals received from IMD 12 or signals to be transmitted to IMD 12. An insulator 58 and an outer conductive cladding 60 surround center conductor 56. Insulator 58 isolates center conductor 56 from electrical interference as well as from outer conductive cladding 60. The thickness of insulator 58 varies depending on the type of coaxial cable used to construct coaxial cable antennas 16 and provides coaxial cable antennas 16 with a characteristic impedance. Conductive cladding 60 may serve as a ground in order to reduce the amount of electrical and radio frequency interference experienced by center conductor 56. Center conductor 56 and conductive cladding 60 may be constructed of conductive materials such as copper, platinum, aluminum and the like. Insulator 58 may be constructed of materials such as PTFE, polyvinyl, polypropylene or the like.

As illustrated in the example of FIG. 4, a portion of outer conductive cladding 60 is removed to expose insulator 58 of coaxial cable antenna 16. The portion of outer conductive cladding 60 that is removed may be located at a midpoint of coaxial cable antenna 16. In the example of FIG. 4, the portion of outer conductive cladding 60 is removed near the respective upper corner of display 20, i.e., proximate the intersection of portion 46 of coaxial cable antenna 16 that is substantially parallel with a side of display 20 and portion 48 of coaxial cable antenna 16 that is substantially parallel with a top of display 20.

Further, a portion of exposed insulator 58 is removed to expose center conductor 56 of coaxial cable antenna 16. In the example illustrated in FIG. 4, the portion of insulator 58 removed is approximately at a midpoint of coaxial cable antenna 16, i.e., near the respective upper corner of display 20. A resistor 62 and a capacitor 64 are coupled to center conductor 56. More particularly, resistor 62 and capacitor 64 are connected between center conductor 56 and outer conductive cladding 60. Capacitor 64 connects to center conductor 56 in order to adjust the voltage standing wave ratio (VSWR) at the center of an operating frequency of coaxial cable antenna 16. Resistor 62 connects to center conductor 56 to lower the quality factor (Q) of coaxial cable antenna 16, in turn, widening the antenna bandwidth in order to achieve simpler matching of coaxial cable antenna 16 and receiver 32 and/or transmitter 34 of RF module 31.

Coaxial cable antenna 16 further includes an end portion 68, which exposes center conductor 56. Coaxial cable antenna 16 can be shear cut to give coaxial cable antenna 16 a particular length. Coaxial cable antenna 16 further includes a hole 66 cutting open center conductor 56 to tune the operating frequency of coaxial cable antenna 16. Hole 66 may be formed, for example, by drilling through coaxial cable antenna 16 until center conductor 56 is cut, but stopping before drilling through the other side of outer conductive cladding 60. Hole 66 may be located between end portion 68 and the removed portion of outer conductive cladding 60. Placement of hole 66 nearer end portion 68 results in a lower operating frequency than placement of hole 66 near the removed portion of outer conductive cladding 60. Hole 66 may be placed such that the operating frequency of coaxial cable antenna 16 is approximately 400 Megahertz (MHz) and, more specifically, approximately 403 MHz. The length of each coaxial cable antennas 16 is based on the desired operating frequency of coaxial cable antennas 16.

Various embodiments of the invention have been described. For example, coaxial cable antennas 16 may be located within a patient monitor that does not have programming capabilities. Coaxial cable antennas 16 may be located within a separate device and attached to programmer 10 via a cable or other connection. Further, although described in terms of an operating frequency of approximately 400 MHz, the coaxial cable antennas of the invention may be scaled in size to operate at different frequencies. These and other embodiments are within the scope of the following claims.

The invention claimed is:

1. A device to communicate with an implanted medical device, the device comprising:
   a first coaxial cable antenna;
   a second coaxial cable antenna; and
   a receiver that receives signals from the implanted medical device via at least one of the first and second coaxial cable antennas.

2. The device of claim 1, further comprising a transmitter that transmits signals to the implanted medical device via at least one of the first and second coaxial cable antennas.

3. The device of claim 1, further comprising a display to convey data received from the implanted medical device to a user.

4. The device of claim 3, wherein the display includes a display housing, and the coaxial cable antennas are mounted within the housing.

5. The device of claim 4, wherein the first and second coaxial cable antennas are located in apposition to one another.

6. The device of claim 5, wherein each of the coaxial cable antennas includes a first portion in substantially parallel orientation with a side of the display and a second portion in substantially parallel orientation with another side of the display.

7. The device of claim 1, wherein each of the coaxial cable antennas includes an outer conductive cladding, and a portion of the outer conductive cladding is removed to expose an insulator of the coaxial cable antenna.

8. The device of claim 7, wherein each of the coaxial cable antennas includes a center conductor, and wherein a portion of the exposed insulator is removed to expose the center conductor of the coaxial cable antenna.

9. The device of claim 8, further comprising a resistor connected between the exposed center conductor of the coaxial cable antenna and the outer conductive cladding of the coaxial cable antenna.

10. The device of claim 8, further comprising a capacitor connected between the exposed center conductor of the coaxial cable antenna and the outer conductive cladding of the coaxial cable antenna.

11. The device of claim 1, wherein each of the coaxial cable antennas comprises a hole that extends partially through coaxial cable antenna to cut through the center conductor of the coaxial cable antennas in order to tune an operating frequency of the antenna.

12. The device of claim 1, wherein each of the coaxial cable antennas includes an center portion that exposes a center conductor of the coaxial cable antenna.

13. The device of claim 1, wherein the .coaxial cable antennas are spaced a fraction of a wavelength apart from one another to achieve spatial diversity.

14. The device of claim 13, wherein the coaxial cable antennas are spaced substantially one-half of a wavelength apart from one another to achieve spatial diversity.

15. The device of claim 1, wherein an operating frequency of the coaxial cable antennas is approximately 403 megahertz.

16. The device of claim 1, wherein the device comprises a programmer for the implanted medical device.

17. The device of claim 1, wherein the device comprises a patient monitor for the implanted medical device.

18. A device to communicate with an implanted medical device, the device comprising:
   a plurality of coaxial cable antennas;
   a receiver to receive signals from the implanted medical device via at least one of the coaxial cable antennas; and
   a device housing, the coaxial cable antennas mounted within the device housing.

19. The device of claim 18, further comprising a transmitter that transmits signals to the implanted medical device via at least one of the coaxial cable antennas.

20. The device of claim 18, further comprising a display to convey program data to a user, and wherein the external device housing comprises a display housing.

21. The device of claim 18, wherein each of the coaxial cable antennas include an outer conductive cladding, and a portion of the outer conductive cladding is removed to expose an insulator of the coaxial cable antenna.

22. The device of claim 21, wherein each of the coaxial cable antennas include a center conductor, and wherein a portion of the exposed insulator is removed to expose the center conductor of each of the coaxial cable antennas.

23. The device of claim 22, further comprising a resistor connected between the exposed center conductor of each of the coaxial cable antennas and the outer conductive cladding of each of the coaxial cable antennas.

24. The device of claim 22, further comprising a capacitor coupled between the exposed center conductor of each of the coaxial cable antennas and the outer conductive cladding of each of the coaxial cable antennas.

25. The device of claim 18, wherein each of the coaxial cable antennas comprise a hole that extends partially through coaxial cable antenna to cut a center conductor in order to tune an operating frequency of the antenna.

26. The device of claim 18, wherein each the coaxial cable antennas includes a middle portion that exposes a center conductor of the coaxial cable antenna.

27. The device of claim 18, wherein each of the coaxial cable antennas includes a first portion and a second portion that are substantially perpendicular to one another to achieve polarization diversity.

28. The device of claim 18, wherein the coaxial cable antennas are spaced a portion of a wavelength apart from one another to achieve spatial diversity.

29. The device of claim 18, wherein the external device comprises a programmer for the implanted medical device.

30. The device of claim 18, wherein the external device comprises a patient monitor for the implanted medical device.

31. A method comprising:
   receiving signals from an implanted medical device via a plurality of coaxial cable antennas; and
   processing the signals from the implanted medical device to analyze information from the implanted medical device.

32. The method of claim 31, further comprising transmitting signals to the implanted medical device via at least one of the coaxial cable antennas.

33. The method of claim 31, further comprising displaying the information from the implanted medical device to a user via a display.

34. The method of claim 33, wherein the display includes a display housing, and the coaxial cable antennas are mounted within the display housing.

35. The method of claim 34, wherein a first coaxial cable antenna is located proximate a top left corner of the display housing and a second coaxial cable antennas is located proximate a top right corner of the display housing.

36. The method of claim 35, wherein each of the coaxial cable antennas includes a first portion substantially parallel with a side of the display and a second portion substantially parallel with a top of the display.

37. The method of claim 31, wherein each of the coaxial cable antennas includes an outer conductive cladding, and a portion of the outer conductive cladding is removed to expose an insulator of the coaxial cable antenna.

38. The method of claim 37, wherein each of the coaxial cable antennas includes a center conductor, and wherein a portion of the exposed insulator is removed to expose the center conductor of the coaxial cable antenna.

39. The method of claim 38, further comprising a resistor connected between the exposed center conductor of the coaxial cable antenna and the outer conductive cladding of the coaxial cable antenna.

40. The method of claim 38, further comprising a capacitor connected between the exposed center conductor of the coaxial cable antenna and the outer conductive cladding of the coaxial cable antenna.

41. The method of claim 31, wherein each of the coaxial cable antennas comprises a hole that extends partially through coaxial cable antenna to cut through the center conductor in order to tune an operating frequency of the antenna.

42. The method of claim 31, wherein the coaxial cable antennas are spaced a fraction of a wavelength apart from one another to achieve spatial diversity.

43. The method of claim 42, wherein the coaxial cable antennas are spaced one-half of a wavelength apart from one another to achieve spatial diversity.

44. The method of claim 31, further comprising:
   receiving program parameters from a user; and
   transmitting the program parameters to the implanted medical device via the coaxial cable antennas.

45. The method of claim 31 wherein the operating frequency of the antennas is adaptable to any frequency by scaling the size of the antennas.

\* \* \* \* \*